US009575035B2

(12) United States Patent  (10) Patent No.: US 9,575,035 B2
Urban et al.  (45) Date of Patent: Feb. 21, 2017

(54) VIBRONIC MEASURING DEVICE

(75) Inventors: Martin Urban, Lorrach (DE); Tobias Brengartner, Emmendingen (DE); Alexander Muller, Sasbach-Jechtingen (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 626 days.

(21) Appl. No.: 13/818,855

(22) PCT Filed: Aug. 9, 2011

(86) PCT No.: PCT/EP2011/063650
§ 371 (c)(1),
(2), (4) Date: Feb. 25, 2013

(87) PCT Pub. No.: WO2012/028426
PCT Pub. Date: Mar. 8, 2012

(65) Prior Publication Data
US 2014/0245834 A1    Sep. 4, 2014

(30) Foreign Application Priority Data

Sep. 3, 2010 (DE) .......................... 10 2010 040 219

(51) Int. Cl.
*G01N 29/40* (2006.01)
*G01F 23/296* (2006.01)
(Continued)

(52) U.S. Cl.
CPC .............. *G01N 29/40* (2013.01); *B25F 5/006* (2013.01); *G01F 23/2965* (2013.01);
(Continued)

(58) Field of Classification Search
CPC ...... G01N 29/40; G01N 9/002; G01N 29/022; G01N 11/16; G01N 29/036;
(Continued)

(56) References Cited

U.S. PATENT DOCUMENTS 6,425,293 B1   7/2002  Woodroffe et al.
7,436,100 B2  10/2008  D'Angelico et al.
(Continued)

FOREIGN PATENT DOCUMENTS

DE   101 61 071 A1   6/2003
DE   101 61 072 A1   6/2003
(Continued)

OTHER PUBLICATIONS

International Preliminary Report on Patentability dated May 24, 2012, issued in Application No. PCT/EP2011/063650, in Rijswijk, Netherlands.
(Continued)

*Primary Examiner* — Laura Martin
*Assistant Examiner* — Rose M Miller
(74) *Attorney, Agent, or Firm* — Bacon & Thomas, PLLC

(57) ABSTRACT

A vibronic measuring device for determining at least one process variable of a medium. Included are: an oscillatable unit; a transmitting/receiving unit, which, by means of a transmission signal, excites the oscillatable unit to execute mechanical oscillations and receives the mechanical oscillations and converts such into an analog, electrical, received signal; and a control/evaluation unit (MC), which receives the analog, received signal, digitizes such and determines the process variable therefrom and which produces the transmission signal. Between the transmitting/receiving unit and the control/evaluation unit, a controllable amplifier is arranged, which receives the received signal and produces an adapted, received signal, and that the control/evaluation unit determines an amplitude of the received signal and, as a function of the determined amplitude, controls the amplifier in such a manner that the amplitude of the adapted, received signal is adapted to a digitizable voltage range predetermined by the control/evaluation unit.

8 Claims, 1 Drawing Sheet

(51) Int. Cl.
*G01N 9/00* (2006.01)
*G01N 11/16* (2006.01)
*G01N 29/02* (2006.01)
*G01N 29/036* (2006.01)
*B25F 5/00* (2006.01)

(52) U.S. Cl.
CPC ...... *G01F 23/2966* (2013.01); *G01F 23/2967* (2013.01); *G01N 9/002* (2013.01); *G01N 11/16* (2013.01); *G01N 29/022* (2013.01); *G01N 29/036* (2013.01); *G01N 2291/02818* (2013.01); *G01N 2291/0427* (2013.01)

(58) Field of Classification Search
CPC .. G01N 2291/02818; G01N 2291/0427; B25F 5/006; G01F 23/2966; G01F 23/2965; G01F 23/2967
USPC ............ 73/290 V, 579, 584, 650, 651
See application file for complete search history.

(56) References Cited

U.S. PATENT DOCUMENTS

| | | | |
|---|---|---|---|
| 7,487,057 | B2 | 2/2009 | Heilig et al. |
| 8,442,782 | B2 | 5/2013 | Meier et al. |
| 2004/0035208 | A1 | 2/2004 | Diaz et al. |
| 2005/0071113 | A1 | 3/2005 | Heilig |
| 2007/0109143 | A1 | 5/2007 | Klofer et al. |
| 2010/0161251 | A1* | 6/2010 | D'Angelico et al. ........... 702/54 |
| 2013/0091946 | A1* | 4/2013 | Knowles ............. G01F 23/2961 73/290 V |

FOREIGN PATENT DOCUMENTS

| | | |
|---|---|---|
| DE | 102 37 931 A1 | 2/2004 |
| DE | 102 55 288 A1 | 7/2004 |
| DE | 10 2004 018 506 A1 | 11/2005 |
| DE | 10 2005 020 862 A1 | 11/2006 |
| DE | 10 2007 008 669 A1 | 8/2008 |
| EP | 1 580 539 A1 | 9/2005 |
| WO | 98/19139 A1 | 5/1998 |
| WO | 03/050479 A1 | 6/2003 |

OTHER PUBLICATIONS

International Preliminary Report on Patentability dated Mar. 14, 2013, issued in Application No. PCT/EP2011/063650, in Geneva, Switzerland.

* cited by examiner

VIBRONIC MEASURING DEVICE

TECHNICAL FIELD

The present invention relates to a vibronic measuring device for determining at least one process variable of a medium, which vibronic measuring device includes: an oscillatable unit; a transmitting/receiving unit, which, by means of a transmission signal, excites the oscillatable unit to execute mechanical oscillations and receives the mechanical oscillations and converts such into an analog, electrical, received signal; and a control/evaluation unit, which receives the analog, received signal, digitizes such and determines the process variable therefrom and which produces the transmission signal. The process variable is a predetermined fill level of the medium in a container and/or the density and/or the viscosity of the medium. The oscillatable unit is preferably an oscillatory fork; it can, however, equally be a membrane or a single rod.

BACKGROUND DISCUSSION

Vibronic measuring devices for determining fill level, density, and/or viscosity of a medium are known in the form of oscillatory forks, membrane oscillators and single rods. Common to these vibronic measuring devices is that they possess an oscillatable unit, which is excited to execute resonant oscillations. The excitation occurs, most often, via piezoelectric elements. Drive elements and the oscillatable unit together form the sensor unit. The mechanical oscillations are converted into electrical, received signals and their frequency, amplitude, and/or phase shift evaluated relative to the excitation signal. This is done advantageously digitally in a microcontroller, which is fed the received signal via an analog-digital converter. The excitation signal can be produced likewise in the microcontroller with a predetermined phase shift relative to the received signal and, for example, fed via a digital-analog converter to the drive elements of the oscillatable unit. The amplitude of the received signal varies as a function of the damping of the oscillations of the oscillatable unit. The sensor unit of vibronic measuring devices possesses, consequently, as a rule, a very high dynamic range. The analog-digital converter must possess a correspondingly high resolution, in order to be able to digitize all signals. The resolution of analog-digital converters integrated into microcontrollers is, however, limited and insufficient for such a high dynamic range, so that the range, in which the measuring device can determine the process variable reliably, is limited.

SUMMARY OF THE INVENTION

An object of the invention is, thus, to provide a vibronic measuring device, which has an expanded measuring range compared with known vibronic measuring devices.

The object is achieved by features including that, between the transmitting/receiving unit and the control/evaluation unit, a controllable amplifier is arranged, which receives the received signal and produces an adapted, received signal, and that the control/evaluation unit determines an amplitude of the received signal and, as a function of the determined amplitude, controls the amplifier in such a manner that the amplitude of the adapted, received signal is adapted to a digitizable voltage range predetermined by the control/evaluation unit.

The controllable amplifier, which is placed in the path of the received signal, effects that the dynamic range of the sensor unit is at least partially compensated. Preferably, the controllable amplifier is arranged directly following the transmitting/receiving unit. The amplitude control of the received signal achieves that the spread of the amplitudes of the input signal of the control/evaluation unit is less. The amplification factor can, in such case, be greater, equal or less than one. In the following, thus, the term 'amplification' can also mean attenuation. The adapting of the amplitude of the received signal to the digitizable voltage range dependent on the embodiment of the control/evaluation unit assures that the signal of the oscillatable unit is digitizable. Preferably, for control, the control/evaluation unit determines the amplitude of the adapted, received signal supplied to it.

A further advantageous effect is achieved in the case of high damping and, thus, very low amplitudes of the received signal. Amplification of the signal already before the filter greatly improves the ratio of signal to noise in the filtered, received signal, so that also in the case of these extreme conditions still a reliable determining of the process variables is possible. In the case of conventional measuring devices, the signal is very small in a high viscosity media, due to the strong damping, so that in-coupled disturbances make the measuring difficult or even impossible. The amplification means that disturbance signals in-coupled after the filter are negligible.

Additionally, the transmission voltage can be so set, either by a digital-analog converter or by an amplifier, that it becomes possible for the amplifier in the receiving path to utilize optimally the range of an analog-digital converter forming the signal input of the control/evaluation unit.

In an embodiment of the measuring device, the control/evaluation unit is a microcontroller, which receives the adapted, received signal via an analog-digital converter. The microcontroller determines the current amplitude of the received signal and adjusts the amplification of the controllable amplifier such that the received signal is digitizable by the analog-digital converter. The amplification factor is greater than one, when the oscillations are greatly damped, and smaller than one, when disturbance signals in-couple, which would exceed the digitizable voltage range. The better the amplitude of the amplified received signal is adapted to the reference voltage of the analog-digital converter, the better is its resolution exploitable and the greater is the bandwidth of evaluable, received signals and, thus, the measuring range. In an embodiment, the control occurs in such a manner that the received signal adapted to the digitizable voltage range has an essentially constant amplitude.

The amplification of the received signal adapted to the control/evaluation unit directly behind the transmitting/receiving unit means that a small resolution of the analog-digital converter is sufficient to digitize the received signals.

In an embodiment of the invention, a filter element, especially a bandpass filter, is arranged between the controllable amplifier and the control/evaluation unit. This filters the wanted signal out from the adapted, received signal.

In an embodiment, the control/evaluation unit includes a digital-analog converter, which supplies the transmission signal to the transmitting/receiving unit.

Associated therewith is an embodiment, in which there is arranged between the digital-analog converter and the transmitting/receiving unit an amplifier with fixed amplification factor, for amplifying the transmission signal. The amplifier enables a greater variation of amplitude.

Another embodiment provides that the control/evaluation unit controls the amplitude of the transmission signal as a function of the amplitude of the received signal in such a manner that the amplitude of the received signal is adaptable to the digitizable voltage range. The control of the transmission voltage is based on the attainable amplification of the controllable amplifier in the receiving path and on the reference voltage of the analog-digital converter. For example, the amplitude of the transmission signal is halved or doubled, in case evaluation of the received amplitude shows that a matching to the digitizable range not is possible.

An embodiment of the invention provides that a second controllable amplifier is arranged between a signal output of the control/evaluation unit for the transmission signal and the transmitting/receiving unit, and that the control/evaluation unit controls the second controllable amplifier as a function of the amplitude of the received signal in such a manner that the amplitude of the received signal is adaptable by the first amplifier to the digitizable voltage range. This embodiment relates especially to the case, in which the transmission signal is not output via a digital-analog converter, since this is likewise suitable for controlling the amplitude of the transmission signal. The amplitude control in the receiving path is optimized based on the amplitude control in the transmission path, since the transmission voltage is adjustable either by a digital-analog converter or by a second controllable amplifier in such a manner that it is possible for the controllable amplifier in the receiving path optimally to utilize the range of the analog-digital converter. For example, the amplitude of the transmission signal is always set in such a manner that the controllable amplifier in the receiving path lies in the middle of its range. Alternatively, the transmission voltage is increased only when the amplitude of the received signal is too small, even after maximum amplification, to be evaluated or when the adapted, received signal cannot optimally utilize the analog-digital converter of the control/evaluation unit.

In an embodiment of the invention, the oscillatable unit is an oscillatory fork. In alternative embodiments, the oscillatable unit is a membrane or a single rod. The process variable is a predetermined fill level of the medium in a container and/or the density and/or the viscosity of the medium.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1:
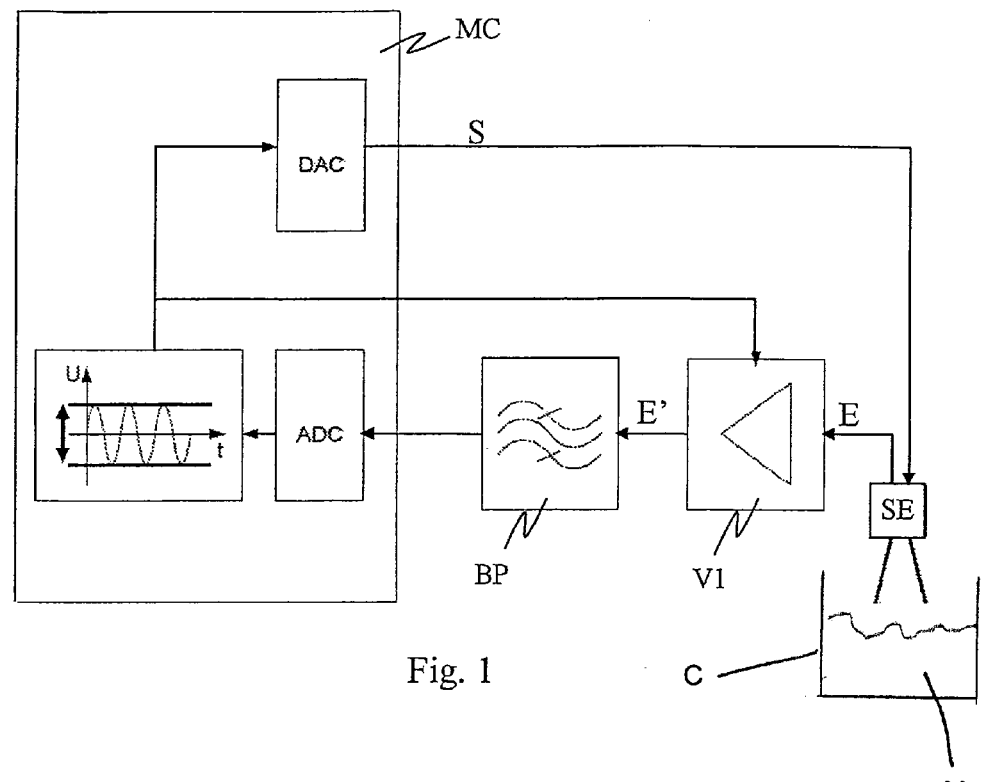
FIG. 1 is the schematic construction of a first embodiment of a control loop with amplitude control.

FIG. 1 shows, schematically, the components of a control loop of a vibronic measuring device. The transmitting/receiving unit TR excites the oscillatable unit to mechanical oscillations and also receives its oscillations. The transmitting/receiving unit TR is connected with the oscillatable unit—here indicated to be an oscillatory fork—and forms therewith the sensor unit of the measuring device. Preferably, the transmitting/receiving unit TR is a piezoelectric transducer, which converts electrical signals into mechanical signals and vice versa. In other embodiments, the transmitting/receiving unit TR can, however, also be electromagnetic or magnetostrictive elements.

The transmitting/receiving unit TR is fed a transmission signal T in the form of an alternating voltage. The mechanical oscillations of the oscillatable unit produce in the transmitting/receiving unit TR an electrical, received signal R, whose amplitude, frequency and phase shift relative to the transmission signal depend on the properties of the medium, in which the oscillation occurs. The evaluation of the received signal R in reference to the process variable to be determined occurs in the control/evaluation unit MC.

The shown receiving branch is different from a receiving branch usual for vibronic measuring devices with digital control, in that the receiving branch here is provided with a supplemental, controllable amplifier A1. Arranged behind the controllable amplifier A1 is a filter element BP, which is preferably a bandpass filter. The received signal R', amplified with an adjustable amplification factor, or gain, is filtered and fed to a microcontroller MC, which functions as control/evaluation unit. The microcontroller MC includes, input side, an analog-digital converter ADC and, output side, a digital-analog converter DAC. The analog-digital converter ADC receives the amplified and filtered, received signal R' and converts it into a digital signal.

Microcontroller MC, on the one hand, evaluates the digital, received signal for determining the process variable, e.g. the reaching of the specified fill level, density, and/or viscosity. On the other hand, it determines the amplitude of the received signal R, respectively the amplitude of the adapted, received signal R' supplied to it, and produces, based thereon, a control signal for adjusting the degree of amplification of the amplifier A1, which control signal it supplies to the amplifier A1. The amplification of the received signal R is controlled in such a manner that a dynamic range of the amplitude of the received signal R obtained from the sensor unit is at least sufficiently compensated such that the resolution of the analog-digital converter ADC is adequate for digitizing all arising, received signals R. In an advantageous embodiment, the control is set in such a manner that the amplitude of the received signal R' coming from the amplifier A1 is constant. The adapting of the amplitude of the received signal R to the digitizable voltage range of the microcontroller MC means that the microcontroller MC receives even in the case of measuring in high viscosity media, which damp the oscillations of the oscillatable unit greatly, a sufficiently large signal for evaluation with reference to the process variable. Moreover, by arranging the amplifier A1 before the filter element BP, the ratio of signal to noise in the filtered received signal R', which the microcontroller MC is fed, is improved.

Preferably, the microcontroller MC determines the current amplitude of the received signal R' supplied it by sampling the received signal R' at predetermined points in time. The points in time are selected in such a manner that the received signal R', while fulfilling a specified phase relationship relative to the transmission signal, exhibits extrema or zero points. The phase selective sampling is described in the published German patent application No. 102009028022 A1.

Furthermore, the microcontroller MC produces the transmission signal T as a function of the received signal R. In order to excite the oscillatable unit to execute oscillations, the oscillatable unit is supplied with a transmission signal T, which has a specified phase shift relative to the received signal R. As a rule, the phase shift is 90°.

In the published German patent application No. 102010030982 A1, an advantageous method for controlling the phase shift between transmission signal T and received signal R to a specified value is described. The received signal R is, for this, as in the case of above cited method, sampled at points in time, at which the received signal R, in the presence of the specified phase shift, assumes an extreme value or has a zero crossing. If the phase shift does not agree with that specified, the sampled voltage values of the received signal R deviate from the desired values. If this is the case, the transmission frequency correlated with the phase shift is readjusted corresponding to the deviation. The measuring device of the invention enables an optimized phase control. If the amplitude of the received signal R is not constant, the amplitude should be continually measured, in order that, in the case of a deviation of the sampled voltage value from the desired value, the required correction can be ascertained. This is based on the fact that the size of the deviation of the sampled voltage value from the desired value depends both on the present phase shift as well as also on the amplitude of the received signal R, so that, without knowledge of the amplitude, the phase shift present is not detectable. In the case of an increasing damping by the medium, this has the result that the phase is too weakly readjusted, i.e. the phase control is too slow. In the case of constant amplitude, this damping dependency of the phase control is absent. The amplitude control with the assistance of the controllable amplifier A1 enables, thus, also in the case of greatly damping media, a phase control with sufficiently high speed.

The microcontroller MC outputs the transmission signal T via the digital-analog converter DAC. The digital-analog converter DAC enables varying of the amplitude of the transmission signal T. Preferably, the amplitude control of the transmission signal T occurs in such a manner that the received signal R occurring as reaction of the oscillatable unit to the transmission signal T has an amplitude, which is adapted optimally to the first controllable amplifier A1. The controllable amplifier A1 can then produce an adapted, received signal R', which fully uses the range of the analog-digital converter ADC in the ideal case. For example, the transmission voltage is so controlled that the amplifier produces the adapted, received signal in the case of a middle amplification factor in such a manner that the level of the adapted, received signal agrees with the level of the reference voltage of the analog-digital converter. As function of the embodiment of the digital-analog converter DAC, it can be required for this that an amplifier AMP be arranged in the transmitting branch, which amplifies the transmission signal T, before it supplies it to the transmitting/receiving unit TR. This amplifier AMP has a fixedly specified amplification factor. An at least approximately fully utilized analog-digital converter ADC is especially advantageous in connection with above described controlling of the phase shift via the detection of deviations in the zero crossing. The high received voltage and the thereby achieved high resolution lead to good resolution of possibly occurring deviations in the zero crossing, which enables a rapidly acting control.

Figure 2:
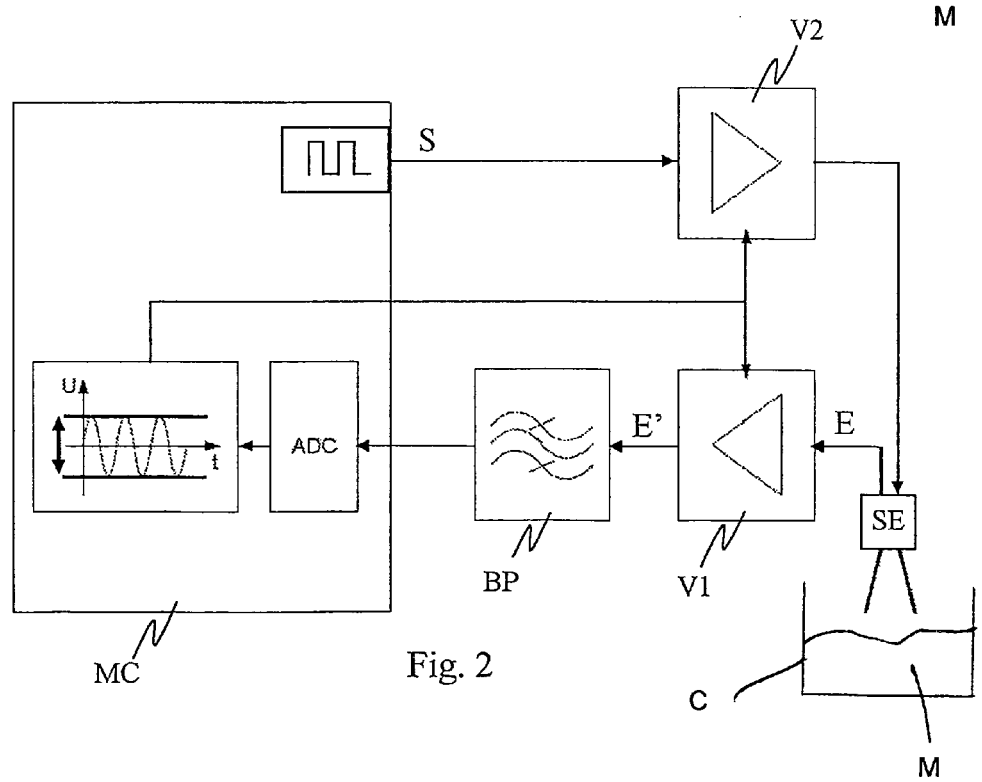
FIG. 2 is the schematic construction of a second embodiment of a control loop with amplitude control.

FIG. 2 discloses an alternative embodiment of the control loop. In contrast to the microcontroller MC illustrated in FIG. 1, the in this case applied microcontroller MC contains no digital-analog converter DAC. The rectangular or sinusoidal transmission signal T is output with constant level from a port and then fed to a second controllable amplifier A2. The amplitude adapting of the transmission signal T to the amplitude of the received signal R dependent on the currently present damping occurs now by means of the controllable amplifier A2 outside of the microcontroller MC. The control signals of the two amplifiers A1 and A2 can, in such case, be transmitted via the same bus. The receiving branch does not differ from the receiving branch illustrated in FIG. 1.

The medium M is shown in a container C shown in FIGS. 1 and 2.

The invention claimed is:

1. A vibronic measuring device for determining at least one process variable of a medium, comprising:
an oscillatable unit;
a transmitting/receiving unit, which, by means of a transmission signal, excites the oscillatable unit to execute mechanical oscillations and receives the mechanical oscillations and converts such into an analog, electrical, received signal; and
a control/evaluation unit, which is a microcontroller, wherein:
between said transmitting/receiving unit and said control/evaluation unit, a controllable amplifier is arranged, which receives the received signal and produces an adapted, received signal; and
said control/evaluation unit receives the adapted, received signal via an analog-digital converter forming the signal input of said control/evaluation unit, which analog-digital converter converts the adapted, received signal into a digital adapted received signal, said control/evaluation unit determines the process variable from the adapted received signal and produces the transmission signal, and said control/evaluation unit determines a current amplitude of the adapted received signal, and, as a function of the determined amplitude, controls said amplifier by adjusting the degree of amplification in such a manner that the amplitude of the adapted, received signal is adapted to a reference voltage of said analog-digital converter.

2. The measuring device as claimed in claim 1, further comprising:
a filter element arranged between said controllable amplifier and said control/evaluation unit.

3. The measuring device as claimed in claim 1, wherein:
said control/evaluation unit has a digital-analog converter, which supplies the transmission signal to said transmitting/receiving unit.

4. The measuring device as claimed in claim 3, wherein:
between said digital-analog converter and said transmitting/receiving unit, an amplifier with fixedly set amplification factor is arranged, which amplifies the transmission signal.

5. The measuring device as claimed in claim 1, wherein:
said control/evaluation unit controls the amplitude of the transmission signal as a function of the amplitude of the received signal in such a manner that the amplitude of the received signal is adaptable to the digitizable voltage range.

6. The measuring device as claimed in claim 5, wherein:
a second controllable amplifier is arranged between a signal output of said control/evaluation unit for the transmission signal and said transmitting/receiving unit; and
said control/evaluation unit controls said second controllable amplifier as a function of the amplitude of the received signal in such a manner that the amplitude of the received signal is adaptable by said first amplifier to the digitizable voltage range.

7. The measuring device as claimed in claim 1, wherein:
said oscillatable unit is one of:
an oscillatory fork, a membrane and a single rod.

8. The measuring device as claimed in claim 1, wherein:
the process variable is one of: a predetermined fill level of the medium in a container and/or the density of the medium and/or the viscosity of the medium.

\* \* \* \* \*